(12) United States Patent
Huang

(10) Patent No.: US 10,113,944 B2
(45) Date of Patent: Oct. 30, 2018

(54) CIRCUIT BOARD TESTING APPARATUS AND CIRCUIT BOARD TESTING METHOD

(71) Applicant: Shenzhen China Star Optoelectronics Technology Co., Ltd., Shenzhen, Guangdong (CN)

(72) Inventor: Xiaoyu Huang, Guangdong (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 146 days.

(21) Appl. No.: 15/118,875

(22) PCT Filed: Jun. 27, 2016

(86) PCT No.: PCT/CN2016/087254
§ 371 (c)(1),
(2) Date: Aug. 13, 2016

(87) PCT Pub. No.: WO2017/201797
PCT Pub. Date: Nov. 30, 2017

(65) Prior Publication Data
US 2018/0113061 A1    Apr. 26, 2018

(30) Foreign Application Priority Data

May 26, 2016 (CN) .......................... 2016 1 0361795

(51) Int. Cl.
*G01N 3/20* (2006.01)
*G01N 3/04* (2006.01)
(Continued)

(52) U.S. Cl.
CPC .................. *G01N 3/20* (2013.01); *G01N 3/04* (2013.01); *G01N 3/36* (2013.01); *G01R 31/28* (2013.01);
(Continued)

(58) Field of Classification Search
CPC .... G01N 3/20; G01N 2203/0023; G01N 3/12; G01N 3/32; G01N 3/36; G01N 3/10; G01N 31/2817
See application file for complete search history.

(56) References Cited

U.S. PATENT DOCUMENTS 5,503,024 A      4/1996  Bechtel et al.
5,567,884 A *  10/1996  Dickinson ................ G01N 3/20
                                                              257/E21.53
(Continued)

FOREIGN PATENT DOCUMENTS

CN       101876409 A      11/2010
CN       203478016 U       3/2014
(Continued)

*Primary Examiner* — Freddie Kirkland, III
(74) *Attorney, Agent, or Firm* — Andrew C. Cheng

(57) ABSTRACT

The present application discloses a circuit board testing apparatus to the printed circuit board, including: a base frame; a carrying platform located on the upper surface of the base frame, the carrying platform including a carrying curved surface, a first distance is formed between the central portion of the carrying curved surface and the upper surface of the base frame, a second distance is formed between the two terminals of the carrying curved surface and the upper surface of the base frame, the second distance is greater than the first distance; and a plurality of supporting components disposed in intervals, each of the supporting components including a supporting rod and a driving member, the driving member is fixed on the base frame, the supporting rods pass through the carrying curved surface, the driving member drives the supporting rod to move in the direction perpendicular to the upper surface, and makes the printed circuit board bending and deformation.

18 Claims, 2 Drawing Sheets

(51) Int. Cl.
*G01R 31/28* (2006.01)
*G01N 3/36* (2006.01)
*G01R 31/44* (2006.01)

(52) U.S. Cl.
CPC ......... *G01R 31/2817* (2013.01); *G01R 31/44* (2013.01)

(56) References Cited

U.S. PATENT DOCUMENTS

| | | | |
|---|---|---|---|
| 5,616,848 A * | 4/1997 | Hemingway | G01N 3/20 73/838 |
| 7,336,087 B2 * | 2/2008 | Korting | G01R 1/07328 324/750.16 |
| 9,194,809 B2 * | 11/2015 | Takagi | G02F 1/1309 |
| 9,354,151 B2 * | 5/2016 | Clark | G01M 5/0075 |
| 2006/0290368 A1 | 12/2006 | Korting et al. | |
| 2014/0307257 A1 * | 10/2014 | Takagi | G02F 1/1309 356/244 |
| 2015/0268144 A1 * | 9/2015 | Clark | G01M 5/0075 73/849 |
| 2016/0086527 A1 * | 3/2016 | Kim | G09G 3/006 324/750.01 |

FOREIGN PATENT DOCUMENTS

| | | |
|---|---|---|
| CN | 104036734 A | 9/2014 |
| CN | 104181057 A | 12/2014 |
| CN | 203981495 U | 12/2014 |
| CN | 204027920 U | 12/2014 |
| CN | 104676389 A | 6/2015 |
| CN | 104916235 A | 9/2015 |
| CN | 105043902 A | 11/2015 |
| JP | 2008-262823 A | 10/2008 |

\* cited by examiner

CIRCUIT BOARD TESTING APPARATUS AND CIRCUIT BOARD TESTING METHOD

CROSS REFERENCE

This application claims the priority of Chinese Patent Application No. 201610361795.8, entitled "CIRCUIT BOARD TESTING APPARATUS AND CIRCUIT BOARD TESTING METHOD", filed on May 26, 2016, the disclosure of which is incorporated herein by reference in its entirety.

FIELD OF THE INVENTION

The present application relates to a circuit board testing technology field, and more particularly to a circuit board testing apparatus and a circuit board testing method by the application of the circuit board testing apparatus.

BACKGROUND OF THE INVENTION

The thin film transistor liquid crystal display, TFT-LCD is one of the main varieties of the flat panel displays currently, and has become an important display platform of the modern IT, video products. The main driving principle of the TFT-LCD is: the R/G/B compressed signal, the control signal and power of the system board is connected to the timing control board via the wires. After the data arranged by the IC chip of the timing controller, TCON on the timing control board, is transmitted to each of the source-chip on film, S-COF and the gate-chip on film, G-COF via the printed circuit board, PCB. The source-chip on film and the gate-chip on film are connected to the display zone of the liquid crystal display, so that the liquid crystal display can obtain the required power and signal.

With the popularity of curved television and other curved surface display, the curved surface applications of TFT-LCD are increasing. Because the curved panels, the elements on the printed circuit board may be sealing off, so it is necessary to perform the bending test to the printed circuit board in advance. The existing test methods are mainly the manual bending test by personnel with low test efficiency.

SUMMARY OF THE INVENTION

The technology problems need to be solved is to provide a circuit board testing apparatus with high testing efficiency and a circuit board testing method by the application of the circuit board testing apparatus for a printed circuit board.

In order to achieve the function mentioned above, the embodiment of the present application adapts the following technology approach:

In an aspect, a circuit board testing apparatus is provided and used in bending test to the printed circuit board, including:

a base frame;

a carrying platform located on the upper surface of the base frame, the carrying platform including a carrying curved surface, a first distance is formed between the central portion of the carrying curved surface and the upper surface of the base frame, a second distance is formed between the two terminals of the carrying curved surface and the upper surface of the base frame, the second distance is greater than the first distance; and a plurality of supporting components disposed in intervals, each of the supporting components including a supporting rod and a driving member, the driving member is fixed on the base frame, the supporting rods pass through the carrying curved surface, one terminal of the supporting rod is used to connect to the printed circuit board, the other terminal of the supporting rod is connected to the driving member, the driving member drives the supporting rod to move in the direction perpendicular to the upper surface, making the different movement by the plurality of the supporting rods, to fit the printed circuit board and the carrying curved surface to each other, and makes the printed circuit board bending and deformation.

Wherein one terminal of the supporting rods further including a snap for fixing the printed circuit board.

Wherein the free path of the supporting rods is greater than the difference between the second distance and the first distance.

Wherein the free path of the supporting rods is smaller than twice of the difference between the second distance and the first distance.

Wherein the driving member is a pneumatic driving member.

Wherein the driving member is a hydraulic driving member.

Wherein the circuit board testing apparatus further including a control means, and the control means is electrically connected to the driving member for controlling the operating state of the driving member.

Wherein the plurality of the supporting component including a first supporting component, a second supporting component, and a third supporting component, wherein the supporting rods of the first supporting component pass through the central portion of the carrying curved surface, the second supporting component and the third supporting component are located on both sides of said first supporting component.

Wherein the carrying curved surface is a curved surface.

In other aspect, a circuit board testing method is provided for the bending test to the printed circuit board is performed by using the circuit board testing apparatus, wherein the circuit board testing method including:

detecting a printed circuit board to form an initial record;

fixing the printed circuit board to the plurality of the supporting components simultaneously;

driving the plurality of the supporting rods to move toward the carrying curved surface to make the printed circuit board fits the carrying curved surface and bending occurs, driving the plurality of the supporting rods to move away from the carrying curved surface, and makes the printed circuit board back straight;

repeating the former action in multiple cycles, such that the printed circuit board bending and back straight in multiple cycles;

detecting the printed circuit board again and forms a second record;

comparing the second record and the initial record, if the second record and the initial record are the same, the printed circuit board passes the bending testing, if the second record and the initial record are different, the printed circuit board fails in the bending testing.

Comparing to the conventional technology, the application has the following advantage:

the circuit board testing apparatus fixes the printed circuit board by all of the plurality of the supporting rods. When the plurality of the supporting rods has different movement, the printed circuit board is bended and deformation, so that the bending test of the circuit board testing apparatus to the printed circuit board is with high efficiency. Meanwhile, each of the supporting rods are all drive by the respective driving member, therefore by adjusting each of the drive member to adjust the movement of each of the correspond supporting rods, such that the different degree of bending of the printed circuit board can be produced, in order to meet the more variety needs of the testing.

BRIEF DESCRIPTION OF THE DRAWINGS

In order to more clearly illustrate the embodiments of the present application or prior art, the following figures will be described in the embodiments are briefly introduced. It is obvious that the drawings are merely some embodiments of the present application, those of ordinary skill in this field can obtain other figures according to these figures without paying the premise.

DETAILED DESCRIPTION OF PREFERRED EMBODIMENTS

Figure 1:
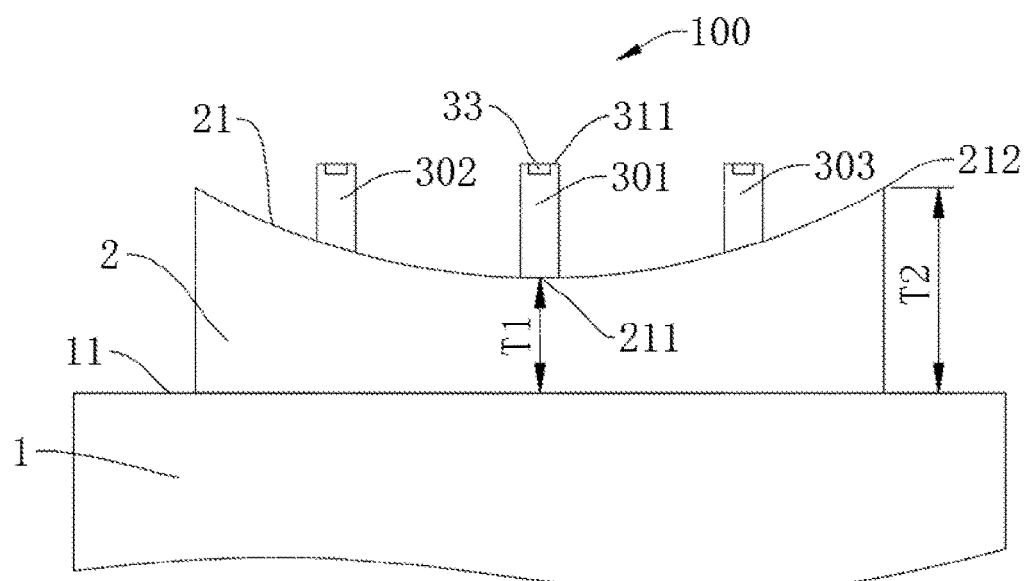
FIG. 1 is a schematic front view of the structure of a circuit board testing apparatus according to an embodiment of the present application.

Embodiments of the present application are described in detail with the technical matters, structural features, achieved objects, and effects with reference to the accompanying drawings as follows. It is clear that the described embodiments are part of embodiments of the present application, but not all embodiments. Based on the embodiments of the present application, all other embodiments to those of ordinary skill in the premise of no creative efforts obtained should be considered within the scope of protection of the present application.

Specifically, the terminologies in the embodiments of the present application are merely for describing the purpose of the certain embodiment, but not to limit the invention. Examples and the claims be implemented in the present application requires the use of the singular form of the book "an", "the" and "the" are intend to include most forms unless the context clearly dictates otherwise. It should also be understood that the terminology used herein that "and/or" means and includes any or all possible combinations of one or more of the associated listed items.

Additionally, the following description of the embodiments with reference to the attached diagram for illustrating particular embodiments may be used to embodiments of the present invention. The direction of the present invention mentioned, for example, "upper", "lower", "front", "rear", "left", "right", "inside", "outside", "side" and so on, can only with reference to the direction of the accompanying drawings. Thus, the terms of the direction used is in order to better and more clearly illustrate and understanding the present invention, rather than indicating device or element or imply referred to must have a specific orientation, with particular orientation construction and operation, and therefore cannot be construed as limiting the present invention.

In the description of the present invention, it should be noted that, unless clearly defined and limited, the term "mounted," "connected," "connected," "disposed on . . . " should be broadly understood. For example, can be fixed connection, can be removable attached or integrally connected; can be mechanically connected; it can be directly connected, or may be connected indirectly through intermediaries, two elements may be in communication with the interior. Those of ordinary skill in the art, the term can be understood that the above circumstances in the specific meaning of the present invention. Further, in the description of the present invention, unless otherwise specified, "plurality" means two or more. If the term "step" in the present specification appear, which means not only a separate step, while no clear distinction with other processes, this step can be realized as long as the intended function is also included in the parlance. In this specification, by "~" indicates the numerical range means that the "-" values before and after, respectively, as described, including the maximum and minimum values of the range. In the drawings, similar or identical structural units represented by the same reference numerals.

Figure 2:
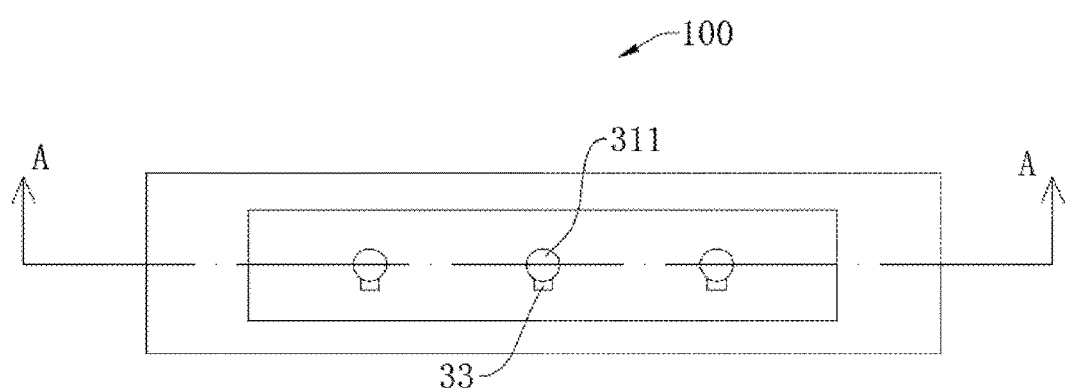
FIG. 2 is a schematic top view of the structure of a circuit board testing apparatus according to an embodiment of the present application.
Figure 3:
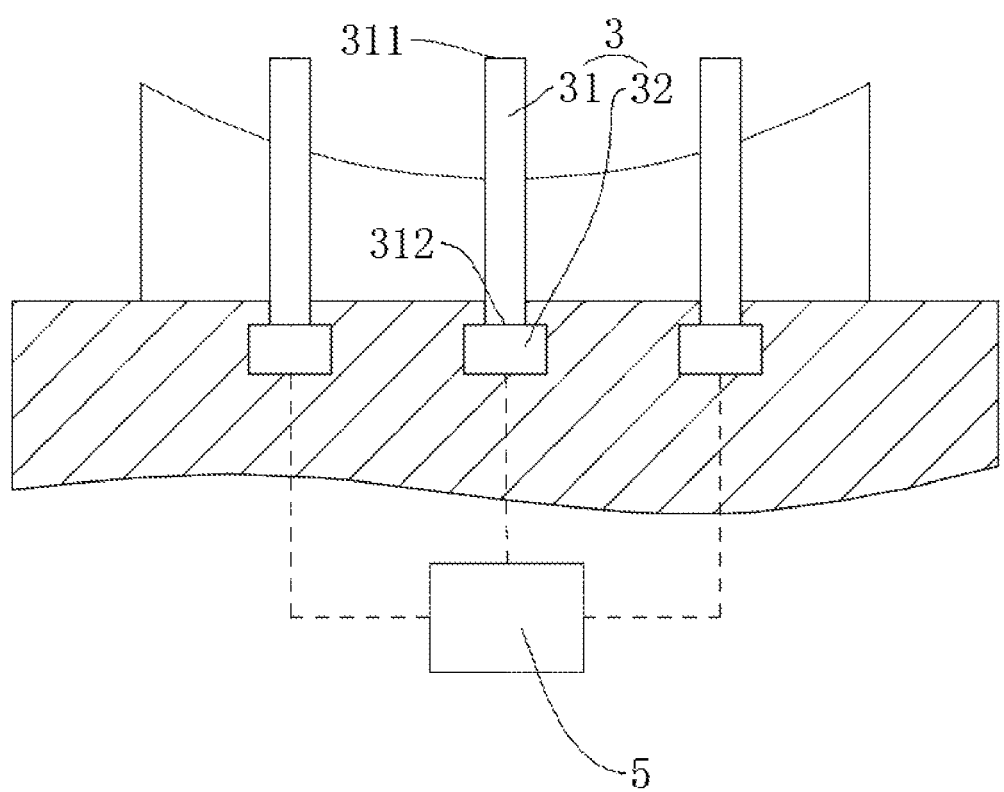
FIG. 3 is a cross-sectional view of A-A site of the structure illustrated in FIG. 2.

Referring to FIGS. 1-3, a circuit board testing apparatus 100 is provided in the embodiment of the present application for the bending test of the printed circuit board (not shown). The circuit board testing apparatus 100 includes a base frame 1, a carrying platform 2, a plurality of supporting components 3. The carrying platform 2 is located on the upper surface 11 of the base frame 1, the carrying platform 2 includes a carrying curved surface 21. A first distance T1 is formed between the central portion 211 of the carrying curved surface 21 and the upper surface 11 of the base frame. A second distance T2 is formed between the two terminals 212 of the carrying curved surface 21 and the upper surface 11 of the base frame, the second distance T2 is greater than the first distance T1. That is, with respect to the two terminals 212, the central portion 211 of the carrying curved surface 21 is recess towards to the upper surface 11. The plurality of the supporting components 3 is disposed in intervals. Each of the supporting components 3 includes a supporting rod 31 and a driving member 32. The driving member 32 is fixed on the base frame 1, the supporting rods 31 pass through the carrying curved surface 21 and are disposed in the different locations of the carrying curved surface 21 in intervals. One terminal 311 of the supporting rod 31 is used to connect to the printed circuit board, the other terminal 312 of the supporting rod 31 is connected to the driving member 32, the driving member 32 drives the supporting rod 31 to move in the direction perpendicular to the upper surface 11. Making the different movement by the plurality of the supporting rods 31, to fit the printed circuit board and the carrying curved surface 21 to each other, so that makes the printed circuit board bending and deformation.

In the present embodiment, the circuit board testing apparatus 100 fixes the printed circuit board by all of the plurality of the supporting rods 31 (the plurality of the supporting rods 31 are fixed in the different positions of the printed circuit board). When the plurality of the supporting rods 31 has different movement, the printed circuit board is bended and deformation, so that the bending test of the circuit board testing apparatus 100 to the printed circuit board is with high efficiency. Meanwhile, each of the supporting rods 31 are all drive by the respective driving member 32, therefore by adjusting each of the drive member 32 to adjust the movement of each of the correspond supporting rods 31, such that the different degree of bending of the printed circuit board can be produced, in order to meet the more variety needs of the testing.

It should be understood that, in this embodiment, the curved shape of the carrying curved surface 21 and the shape of the printed circuit board of practical applications to be tested (such as in a curved surface display) is the same or similar. In the application of the circuit board testing apparatus 100 of the printed circuit board bending test, the supporting rods 31 can be allowed to move to the lowest site toward to the carrying curved surface 21 (in this case, one terminal 311 of the supporting rods 31 is roughly fit with the position of the carrying curved surface 21), such that the printed circuit board fit with the carrying curved surface 21, the degree of the bending of the printed circuit board and its environment in practical applications is the closest, and is beneficial to improve the accuracy of the bending test of the printed circuit board. And, in order to meet the commonly testing requirements to the environment of various curved application, the connection relation of the carrying platform 2 and the base frame 1 can be a detachable connection, i.e., the circuit board testing apparatus 100 can switch to a different carrying platform 2 to meet more testing needs.

For example, the carrying curved surface 21 is a curved surface, the curvature of the curve and the curvature of said printed circuit board to be tested in the environment of the actual practical application is the same. Of course, in other embodiments, the carrying curved surface 21 can be a parabolic surface, V- or U-shaped curved surfaces and the like.

Further, please also referring to FIGS. 1 to 3, as an alternative embodiment, one terminal 311 of the supporting rods 31 has a snap 33 for fixing the printed circuit board. Of course, since the supporting rods 31 is provided with a snap 33, it can prevent the terminal 311 of the supporting rods 31 shift from the side of the carrying curved surface 21 to another side to damage the printed circuit board to be tested.

Further, please also referring to FIGS. 1 to 3, as an alternative embodiment, the free path of the supporting rods 31 is greater than the difference between the second distance T2 and the first distance T1, T=T2-T1, i.e. during the movement of the supporting rods 31, the maximum distance between the supporting rods 31 and the upper surface 11 of the base frame 1 is larger than the second distance T2. Therefor the supporting rods 31 has a sufficiently long free path, and can control the bending of the carrying curved surface 21 to fit the printed circuit board, or completely remote from the carrying curved surface 21 to restore straight.

Preferably, the free path of the supporting rods 31 is smaller than twice of the difference between the second distance T2 and the first distance T1. At this time, by the cooperation of each of the plurality of the supporting rods 31, the printed circuit board can achieve bending and deformation in two opposite directions.

Further, as an alternative embodiment, the driving member 32 is a pneumatic driving member or a hydraulic driving member, with energy efficiency and accuracy. By using the plurality of supporting rods 31, the printed circuit board to be tested can complete the predetermined action to be bent and back straight. Of course, in other embodiments, the driving member 32 can be an electric driving member or a mechanical driving member.

Further, referring to FIG. 3, in order to improve the control accuracy of the movement of the plurality of the supporting rods 31, the circuit board testing apparatus 100 further includes a control means 5, the control means 5 is electrically connected to the driving member 32 for controlling the operating state of the driving member 32. The control means 5 includes a processor configured by software to calculate the movement of each of the supporting rods 31 and the corresponding operating parameters of the driving member 32.

Further, referring to FIGS. 1 to 3, as a preferred embodiment, the plurality of the supporting components 3 includes a first supporting component 301, a second supporting component 302, and a third supporting component 303, the supporting rods 31 of the first supporting component 301 pass through the central portion 211 of the carrying curved surface 21, the second supporting component 302 and the third supporting component 303 are located on both sides of said first supporting component 301. In the present embodiment, the first supporting component 301 can be used to support the central of the printed circuit board to be test, the second supporting component 302 and the third supporting component 303, can be used to support the two sides of the printed circuit board to be test, respectively. By the joint action of the first supporting component 301, the second supporting component 302, and the third supporting component 303, can be easily and quickly makes the printed circuit board bending and back to straight, and makes the circuit board testing apparatus 100 with high test efficiency.

A circuit board testing method is further provided in the embodiments of the present application for the bending test to the printed circuit board. The circuit board testing method uses the circuit board testing apparatus 100 (please also referring to FIGS. 1 to 3) as one of the embodiments described above to perform the testing, the circuit board testing method including:

Step 1: detecting a printed circuit board to form an initial record;

Step 2: fixing the printed circuit board to the plurality of the supporting components simultaneously;

Step 3: driving the plurality of the supporting rods to move toward the carrying curved surface to make the printed circuit board fits the carrying curved surface and bending occurs, driving the plurality of the supporting rods to move away from the carrying curved surface, and makes the printed circuit board back straight;

Step 4: repeating the former action (i.e. Step 3) in multiple cycles, such that the printed circuit board bending and back straight in multiple cycles;

Step 5: detecting the printed circuit board again and forms a second record;

Step 6: comparing the second record and the initial record, if the second record and the initial record are the same, the printed circuit board passes the bending testing, if the second record and the initial record are different, the printed circuit board fails in the bending testing.

The circuit board testing method of the present embodiment, since the printed circuit board is in the operation of bending and back straight in multiple cycles by the adaption of the circuit board testing apparatus 100, the testing efficiency is high, and with high accuracy. It is help for the detection of the yield of the printed circuit board, and better to the applications in the market.

Further, in Step 2, the printed circuit board is fixed in one terminal 311 of the plurality of the supporting rods 31 by the snap 33 in the circuit board testing apparatus 100.

Further, in Step 3 and Step 4, the position, movement and speed of the plurality of the supporting rods 31 can be through the pre-calculated and predetermined to improve the accuracy of the testing.

Further, in Step 1 and Step 5, the detection of the printed circuit board includes a visual inspection and electrical testing.

Above are embodiments of the present application, which does not limit the scope of the present application. Any modifications, equivalent replacements or improvements within the spirit and principles of the embodiment described above should be covered by the protected scope of the invention.

What is claimed is:

1. A circuit board testing apparatus used in a bending test to a printed circuit board, wherein the circuit board testing apparatus comprises:
a base frame;
a carrying platform located on an upper surface of the base frame, the carrying platform comprising a carrying curved surface, a first distance is formed between a central portion of the carrying curved surface and the upper surface of the base frame, a second distance is formed between two terminals of the carrying curved surface and the upper surface of the base frame, the second distance is greater than the first distance; and
a plurality of supporting components disposed in intervals, each of the supporting components comprising a supporting rod and a driving member, the driving member being fixed on the base frame, the supporting rods passing through the carrying curved surface, one terminal of the supporting rod being used to connect to the printed circuit board, another terminal of the supporting rod being connected to the driving member, the driving member driving the supporting rod to move in a direction perpendicular to the upper surface, and the driving member driving the supporting rod to move a displacement to fit the printed circuit board to the carrying curved surface so that the printed circuit board is bent and deformed.

2. The circuit board testing apparatus according to claim 1, wherein one terminal of the supporting rods further comprises a snap for fixing the printed circuit board.

3. The circuit board testing apparatus according to claim 1, wherein a free path of the supporting rods is greater than the difference between the second distance and the first distance.

4. The circuit board testing apparatus according to claim 1, wherein a free path of the supporting rods is smaller than twice of the difference between the second distance and the first distance.

5. The circuit board testing apparatus according to claim 1, wherein the driving member is a pneumatic driving member.

6. The circuit board testing apparatus according to claim 1, wherein the driving member is a hydraulic driving member.

7. The circuit board testing apparatus according to claim 1, wherein the circuit board testing apparatus further comprises a control means, and the control means is electrically connected to the driving member for controlling an operating state of the driving member.

8. The circuit board testing apparatus according to claim 1, wherein the plurality of supporting components comprises a first supporting component, a second supporting component, and a third supporting component, wherein the supporting rods of the first supporting component pass through the central portion of the carrying curved surface, the second supporting component and the third supporting component are located on both sides of said first supporting component.

9. The circuit board testing apparatus according to claim 1, wherein the carrying curved surface is a curved surface.

10. A circuit board testing method for the bending test to the printed circuit board is performed by using the circuit board testing apparatus according to claim 1, wherein the circuit board testing method comprises:
detecting the printed circuit board to form an initial record;
fixing the printed circuit board to the plurality of supporting components simultaneously;
driving the supporting rod of each of the plurality of supporting components to move toward the carrying curved surface to make the printed circuit board fits the carrying curved surface so that the printed circuit board is bent, and driving the supporting rod of each of the plurality of supporting components to move away from the carrying curved surface so that the printed circuit board is back to straight;
repeating the former action in multiple cycles, such that the printed circuit board is bent and back to straight in multiple cycles;
detecting the printed circuit board again and forms a second record;
comparing the second record and the initial record, if the second record and the initial record are the same, the printed circuit board passes the bending testing, if the second record and the initial record are different, the printed circuit board fails in the bending testing.

11. The circuit board testing method according to claim 10, wherein one terminal of the supporting rods further comprises a snap for fixing the printed circuit board.

12. The circuit board testing method according to claim 10, wherein a free path of the supporting rods is greater than the difference between the second distance and the first distance.

13. The circuit board testing method according to claim 10, wherein a free path of the supporting rods is smaller than twice of the difference between the second distance and the first distance.

14. The circuit board testing method according to claim 10, wherein the driving member is a pneumatic driving member.

15. The circuit board testing method according to claim 10, wherein the driving member is a hydraulic driving member.

16. The circuit board testing method according to claim 10, wherein the circuit board testing apparatus further comprises a control means, and the control means is electrically connected to the driving member for controlling the operating state of the driving member.

17. The circuit board testing method according to claim 10, wherein the plurality of the supporting components comprises a first supporting component, a second supporting component, and a third supporting component, wherein the supporting rods of the first supporting component pass through the central portion of the carrying curved surface, the second supporting component and the third supporting component are located on both sides of said first supporting component.

18. The circuit board testing method according to claim 10, wherein the carrying curved surface is a curved surface.

* * * * *